(12) United States Patent
Kondo (10) Patent No.: US 6,409,705 B1
(45) Date of Patent: Jun. 25, 2002

(54) NEEDLE PROTECTING CAP AND NEEDLE DISPOSAL INSTRUMENT

(75) Inventor: Chikashi Kondo, Fukuoka (JP)

(73) Assignees: Noboro Hakozaki; Hideaki Yamada, both of Fukuoka-Ken; Kazuhisa Matsumoto, Ehime-ken; Chisho Hagio, Fukuoka-Ken, all of (JP)

( * ) Notice: Subject to any disclaimer, the term of this patent is extended or adjusted under 35 U.S.C. 154(b) by 0 days.

(21) Appl. No.: 09/463,752

(22) PCT Filed: Aug. 3, 1998

(86) PCT No.: PCT/JP98/03466

§ 371 (c)(1),
(2), (4) Date: Jan. 27, 2000

(87) PCT Pub. No.: WO99/07423

PCT Pub. Date: Feb. 18, 1999

(51) Int. Cl.[7] ................................................ A61M 5/32
(52) U.S. Cl. ....................................................... 604/192
(58) Field of Search ................. 604/192, 263, 604/187, 110; 206/365

(56) References Cited

U.S. PATENT DOCUMENTS 4,973,315 A * 11/1990 Sincock ...................... 604/192
5,047,019 A * 9/1991 Sincock ...................... 604/192

FOREIGN PATENT DOCUMENTS

| JP | 60187735 | 12/1985 |
| JP | 6476873 | 3/1989 |
| JP | 1317453 | 12/1989 |
| JP | 430545 | 3/1992 |
| JP | 425139 | 6/1992 |
| JP | 67447 | 1/1994 |
| JP | 6121836 | 5/1994 |
| JP | 6154325 | 6/1994 |
| JP | 3016719 | 7/1995 |
| JP | 7275360 | 10/1995 |
| JP | 889573 | 4/1996 |

* cited by examiner

Primary Examiner—Manuel Mendez
(74) Attorney, Agent, or Firm—Jordan and Hamburg LLP

(57) ABSTRACT

A needle protecting cap (10) formed of a cylindrical body (11) having an insertion port (12) for an injection needle at one end thereof and capable of holding the injection needle, wherein a slit (15) is formed from the distal end of an insertion notch (13), which has been formed by longitudinally cutting a peripheral wall (11a) inclusive of the insertion port (12) from the side of the insertion port toward the distal end thereof, toward the other end of the cylindrical body; and a needle disposal instrument (60) equipped with a case body (61) that accommodates a plurality of the needle protecting caps (10) and holds the needle protecting caps (10) in such a posture that used injection needles can be inserted from the insertion port (12), and an open/close cover (62) for preventing the needle protecting caps attached to the case body (61) from falling out. The needle protecting cap (10) and the needle disposal instrument (60) permit disposal of a winged needle (51) as well as an ordinary injection needle (50), and also permit efficient disposal of a large quantity of injection needles.

14 Claims, 9 Drawing Sheets

NEEDLE PROTECTING CAP AND NEEDLE DISPOSAL INSTRUMENT

TECHNICAL FIELD

The present invention relates to a needle protecting cap and a needle disposal instrument that enable used injection needles to be safely disposed of without a risk of inadvertent piercing of fingers or the like.

BACKGROUND ART

In recent years, "accidental needle piercing" in which doctors or nurses inadvertently pierce their fingers or the like with injection needles after used for patients has become an issue. In fact, a few thousand of such accidents have been reported all over Japan. The accidental needle piercing develops into serious incidents that put the lives of doctors or nurses at risk if the needles have been used for patients infected by AIDS (HIVE), hepatitis B, hepatitis C, or the like.

Accidental needle piercing most frequently takes place when disposing of used injection needles. Generally, in order to avoid risks caused by disposing of naked injection needles, protecting caps are used to cover distal ends of the injection needles before discarding them.

The protecting caps, however, have small diameters ranging from a few millimeters up to about 10 mm, depending on injection needles for which the caps are used. Hence, when attaching the cap to the needle by inserting a distal end of the needle in an aperture formed in one end of the cap, the distal end frequently fails to be properly inserted into the small aperture, causing the distal end to pierce a finger holding the protecting cap.

To solve such a problem, various kinds of needle protecting caps or associated instruments thereof have been proposed as disclosed in Japanese Unexamined Patent Publication No. 1-76873, Japanese Unexamined Patent Publication No. 6-121836, Japanese Unexamined Patent Publication No. 6-154325, Japanese Unexamined Patent Publication No. 7-275360, Japanese Unexamined Patent Publication No. 8-89573, Japanese Unexamined Utility Model Publication No. 60-187735, etc.

Japanese Unexamined Patent Publication No. 1-76873 discloses a needle protecting cap provided with a guard at the end thereof. With this arrangement, if an injection needle misses an insertion port when inserting the needle in the protecting cap, fingers holding the protecting cap are protected by the guard.

Japanese Unexamined Patent Publication No. 6-121836 discloses a needle protecting cap provided with a lever making use of an action of a lever or a wedge. The lever is held when inserting a needle into the cap so as to keep a distance between the needle and a finger tip, making it possible to prevent accidents of fingers touching the distal ends of needles or accidents of stabbing finger tips.

Japanese Unexamined Patent Publication No. 8-89573 discloses a needle protecting cap in which a part of its shank is provided with a vertically split groove having a width to allow a needle end to be inserted. A needle is inserted in the protecting cap so that the entire needle is dropped along the vertically split groove. With this arrangement, the needle cannot be moved in a direction to pierce a finger, thus making it possible to prevent accidental needle piercing.

Japanese Unexamined Utility Model Publication No. 60-187735 discloses a needle guide groove formed in a side surface of a needle port section. A side surface of the needle is applied to the needle guide groove and pulled away from a needle end to drop the needle end into an insertion port, and then the needle end is inserted in a main body portion. This arrangement makes it possible to prevent the needle end from missing the insertion port at the time of attaching, thereby preventing accidents in which a hand or a finger is stabbed by the needle end.

Thus, diverse attempts have been made in the past to prevent accidental needle piercing, and have been effective in their own way in disposal of ordinary injection needles.

However, none of the protecting caps proposed in the publications described above are suitable for disposal of winged injection needles, although they are suitable for disposal of ordinary injection needles in which the caps are attached to the distal ends of the needle main bodies.

The winged needles are mainly used for drip, and has a pair of butterfly-shaped resilient wings provided on both sides of the needles. As injection can be implemented by holding the wings, it is no longer necessary to attach a needle to a syringe. This arrangement makes it possible to reduce risks of infection and to enable secure fixation of the needle so as to allow stable drip in longer time.

In every one of the protecting caps set forth above, the protecting cap must be taken out for each needle to be disposed of and held by fingers to attach it to the needle. Especially in a large hospital where hundreds of injection needles are used daily, the protecting caps are inconvenient for storage and inefficient and difficult in disposal when they are used in succession.

An object of the present invention is to provide a protecting cap that permits disposal of winged injection needles as well as ordinary injection needles, and to further provide a needle disposal instrument that permits efficient disposal of a large quantity of needles.

DISCLOSURE OF INVENTION

A needle protecting cap in accordance with the present invention is a needle protecting cap comprising a cylindrical body having an insertion port at one end thereof and is capable of holding an injection needle. A peripheral wall inclusive of the insertion port is cut from the side of the insertion port toward the distal end to form a longitudinal elongated notch, and a slit is formed which extends from a distal end of the notch toward the other end of the cylindrical body, or a locking portion for locking a winged needle which is oriented toward the insertion port is formed at the distal end of the notch.

To use the protecting cap in accordance with the present invention for an ordinary syringe needle, the needle is set so that it is substantially parallel to an upper part of the notch, and, in this state, the needle is moved in a direction at right angles to an axis of the protecting cap, and then inserted in the protecting cap from the notch. The needle is further slid toward the distal end of the protecting cap to install the needle in the protecting cap. In the case of a winged needle, the needle is inserted from the notch and slid forward, and the wings are pinched in the slit to lock them or in the locking portion to place the needle in the protecting cap.

Thus, the needle can be placed in the protecting cap without largely moving the needle in its axial direction, thereby preventing accidental finger piercing with conventional protecting caps designed to be held by fingers. Moreover, the protecting cap also allows winged needles to be placed in the cap as safely as in the case of ordinary needles, which has been impossible with the conventional protecting caps.

When a winged needle is locked by pinching it in the slit, a total length of the notch and the slit of the protecting cap mentioned above, or a length of the notch for locking the winged needle by pinching it in the locking portion, is preferably one third or more of a length of a needle used. If the notch is excessively short for the length of the needle, then the distal end of the needle tends to jut out of the protecting cap when the needle is inserted into the notch and slid toward the distal end of the cap.

The same materials used for the conventional protecting caps may be used for the protecting cap. Preferably, however, a resilient durable synthetic resin is used for the slit portion or the locking portion formed at the distal end of the notch. In addition, it is preferable to form the slit and the locking portion by cutting a part of the cylindrical body of the protecting cap. This permits easy mass production making use of conventional products.

Preferably, the slit for locking the winged needle formed so as to extend from the distal end of the notch to the other end of the cylindrical body and the locking portion for locking the winged needle formed at the distal end of the notch are provided with means for preventing the winged needle from falling out. The means for preventing the needle from falling out may be formed by mechanically knurling the surface which contacts the winged needle, or by making the contacting surface highly adhesive.

Furthermore, a slit which can be expanded in a direction in which the insertion port spreads may be formed in the peripheral wall of the insertion port. Forming such a slit enables an end portion of the insertion port to resiliently spread, permitting easy insertion of a proximal end of a needle regardless of the size of the needle.

A ridge line of the peripheral wall defining an outer edge of the longitudinal notch formed by cutting the peripheral wall inclusive of the insertion port from the side of the insertion port toward the distal end thereof may be shaped so as to form a narrow portion at the insertion port. With this arrangement, an inserted needle can be securely retained without a danger of falling out.

A needle disposal instrument in accordance with the present invention that includes the protecting cap set forth above and permits efficient use of the needle protecting cap comprising the cylindrical body having the insertion port at one end thereof and capable of holding a needle is provided with a case body that accommodates a plurality of needle protecting caps, each of the caps being formed of a cylindrical body having an insertion port at one end thereof and capable of holding a needle, and holds the needle protecting caps in such a posture that used needles can be inserted from the insertion ports, and further provided with means for preventing the needle protecting caps attached to the case body from falling out.

The means for preventing the falling out is preferably an open/close cover fitted to the case body on the side of the insertion ports for the needle protecting caps accommodated in the case body. Installing the open/close cover on the side of the insertion ports of the protecting caps makes it possible to prevent the protecting caps from falling out and also to prevent needles placed in the protecting caps from falling out.

In the needle disposal instrument in accordance with the present invention before use, a plurality of empty protecting caps are accommodated in the case body, and the insertion ports of the protecting caps are covered by the cover for preventing falling out. To use the needle disposal instrument, the fall-out preventing cover is opened, and a needle is inserted from the insertion port of the protecting cap and settled in the protecting cap. When all the accommodated protecting caps are filled with needles, the protecting caps are removed from the needle disposal instrument and placed in another container.

At this time, providing a handle at a position away from the position where the open/close cover for preventing the case body from falling out is fit enables a needle to be settled in the protecting cap while holding the handle by a hand. This also makes it possible to keep a distance between the needle and fingers holding the handle, contributing to the prevention of accidental needle piercing. In addition, providing a stand for the case body to support itself will securely prevent accidental needle piercing because a hand or fingers will not be positioned in front of a needle when attaching it to the protecting cap.

The needle disposal instrument may be equipped with a case body which accommodates a plurality of needle protecting caps, the case body maintaining a posture of the accommodated needle protecting caps so that notches of the needle protecting caps are exposed for allowing used injection needles or winged needles to be inserted and having a removal port through which the needle protecting caps can be taken out one by one and urging means for urging the accommodated needle protecting caps toward the removal port.

In the above needle disposal instrument, the protecting caps installed in the needle disposal instrument are mounted on distal ends of ordinary injection needles or winged needles according to the procedure described above and then removed from the needle disposal instrument. With this arrangement, the accommodated protecting caps are pushed out to the removal port in sequence by the urging means, enabling the protecting caps to be mounted onto the next injection needle or winged needle in sequence.

Thus, the arrangement not only permits successive use, but also permits an injection needle or a winged needle to be settled in the protecting caps while holding the case body or the handle provided on the case body by a hand. Hence, the distance between the injection needle or the winged needle and fingers holding the case body can be kept, contributing to the prevention of accidental needle piercing as well.

BRIEF DESCRIPTION OF DRAWINGS

FIG. 2(a) is a sectional view taken along the line A—A of FIG. 1, and (b) and (c) show a state of an insertion port when an injection needle has been inserted.

BEST MODE FOR CARRYING OUT THE INVENTION

Figure 1:
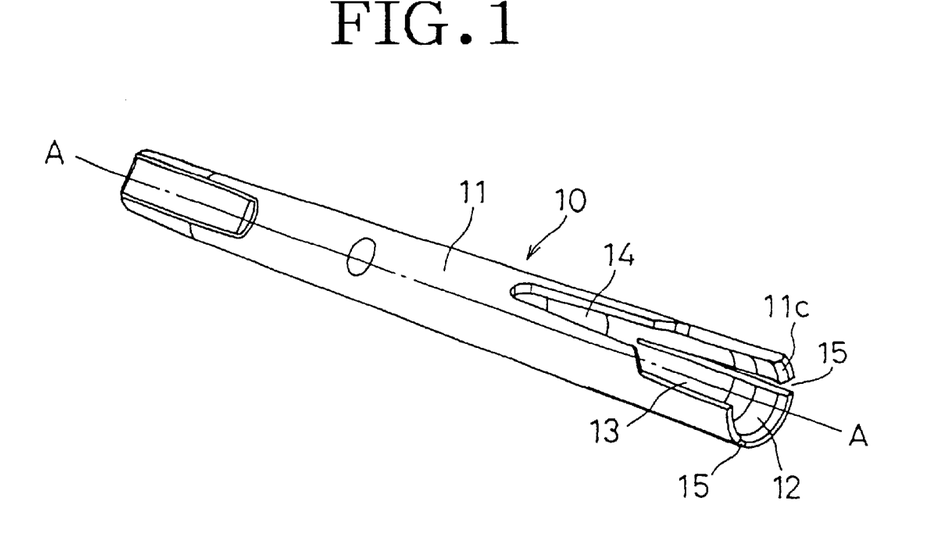
FIG. 1 is a perspective view showing a first embodiment of a needle protecting cap in accordance with the present invention.
Figure 2:
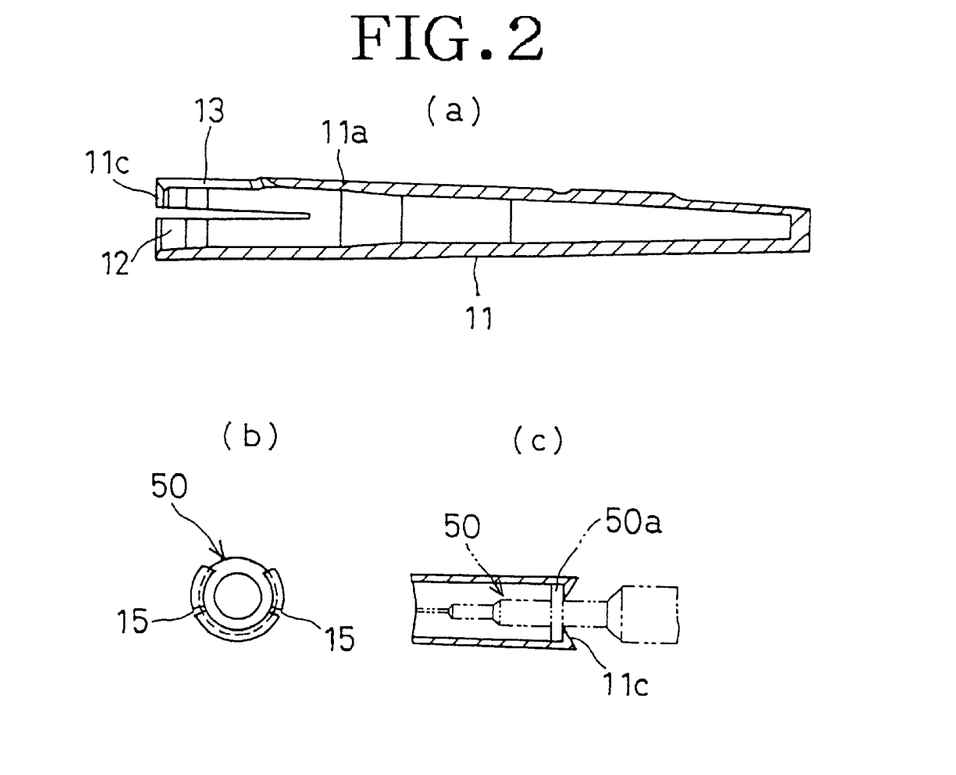

FIG. 1 is a perspective view showing a first embodiment of a needle protecting cap in accordance with the present invention. FIG. 2(*a*) is a sectional view taken along the line A—A of FIG. 1, and (*b*) and (*c*) show a state of an insertion port after a needle is inserted.

A needle protecting cap 10 of the embodiment has an insertion notch 13 in an upper surface of a tapered cylindrical body 11, the insertion notch 13 being formed by longitudinally cutting a peripheral wall 11*a*, which includes an insertion port 12, from the side of the insertion port 12 toward a distal end of the cylindrical body. To permit easy insertion of an injection needle 50, the length of the insertion notch 13 is set to approximately 18% of the cylindrical body 11 in this embodiment. Further, as shown in (*c*) of FIG. 2, an end surface 11*c* of the insertion port 12 is shaped like a hook.

This makes it possible to maintain the size of the insertion notch 13 allowing easy insertion of the injection needle 50 through the insertion notch 13, and, at the same time, to securely hold the injection needle 50 by the end surface 11*c* of the insertion port 12 without a danger of falling out.

Reference numeral 14 denotes a slit formed at a distal end of the insertion notch 13 so that it extends toward a distal end of the cylindrical body 11. The cylindrical body 11 of this embodiment is made of a synthetic resin so that the slit 14 is resilient, thus permitting wings of a winged needle to be pinched and locked by the slit 14. In this embodiment, to ensure easy insertion of the injection needle 50, the total length of the slit 14 and the insertion notch 13 is set to approximately 37% of the cylindrical body 11. Reference numeral 15 shown in FIG. 1 and FIG. 2(*b*) denotes slits formed in the peripheral wall adjacent to the insertion port 12. Forming the slits 15 allows an end adjacent to the insertion port 12 to be elastically expanded as shown in FIG. 2(*b*) so that a proximal end 50*a* of the injection needle 50 can be easily inserted regardless of the size of a needle.

Figure 3:
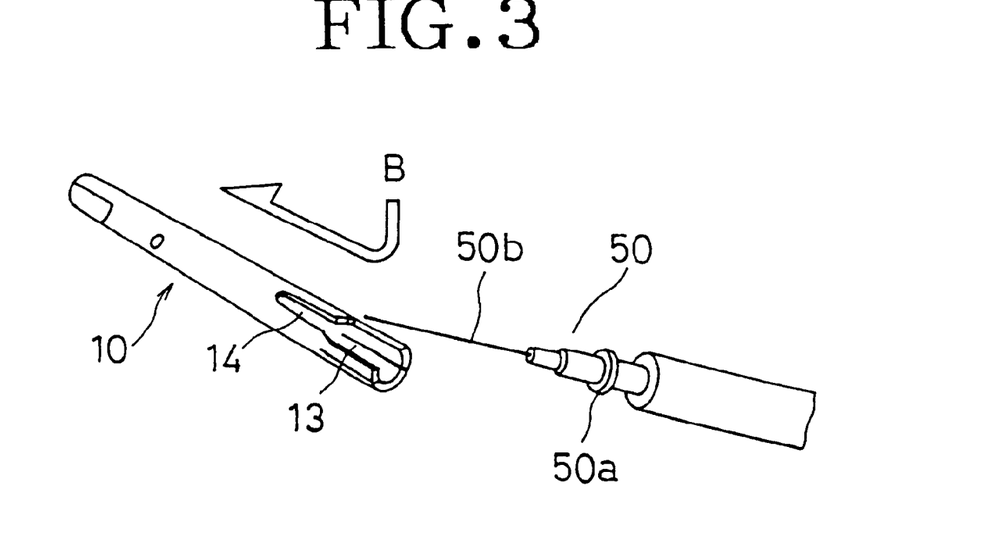
FIG. 3 is a schematic representation illustrating usage of the needle protecting cap of FIG. 1.

To attach the needle 50 to the protecting cap 10, in the case of a needle for an ordinary syringe, a needle 50*b* of the injection needle 50 is placed above the insertion notch 13, and in this state, the needle 50*b* is moved in a direction at right angle to an axis of the injection needle 50, inserted into the protecting cap 10 through the insertion notch 13, and further slid toward the distal end of the protecting cap 10 (in a direction indicated by an arrow B of FIG. 3) to thereby settle the injection needle 50 in the protecting cap 10, as shown in FIG. 3.

FIGS. 2(*b*) and (*c*) are diagrams illustrating a state wherein the injection needle 50 has been settled in the protecting cap 10. As shown in (*b*) of the drawing, even if the proximal end 50*a* of the injection needle 50 is slightly larger, the slits 15 formed in the peripheral wall of the end on the side of the insertion port 12 of the cylindrical body 11 spread to adjust to it. Moreover, since the end surface 11*c* of the insertion port 12 is shaped like a hook as illustrated in (*c*) of the drawing, the proximal end 50*a* of the injection needle 50 can be retained by the end surface 11*c* to hold the injection needle 50 so as to prevent the needle 50 from falling out.

Figure 4:
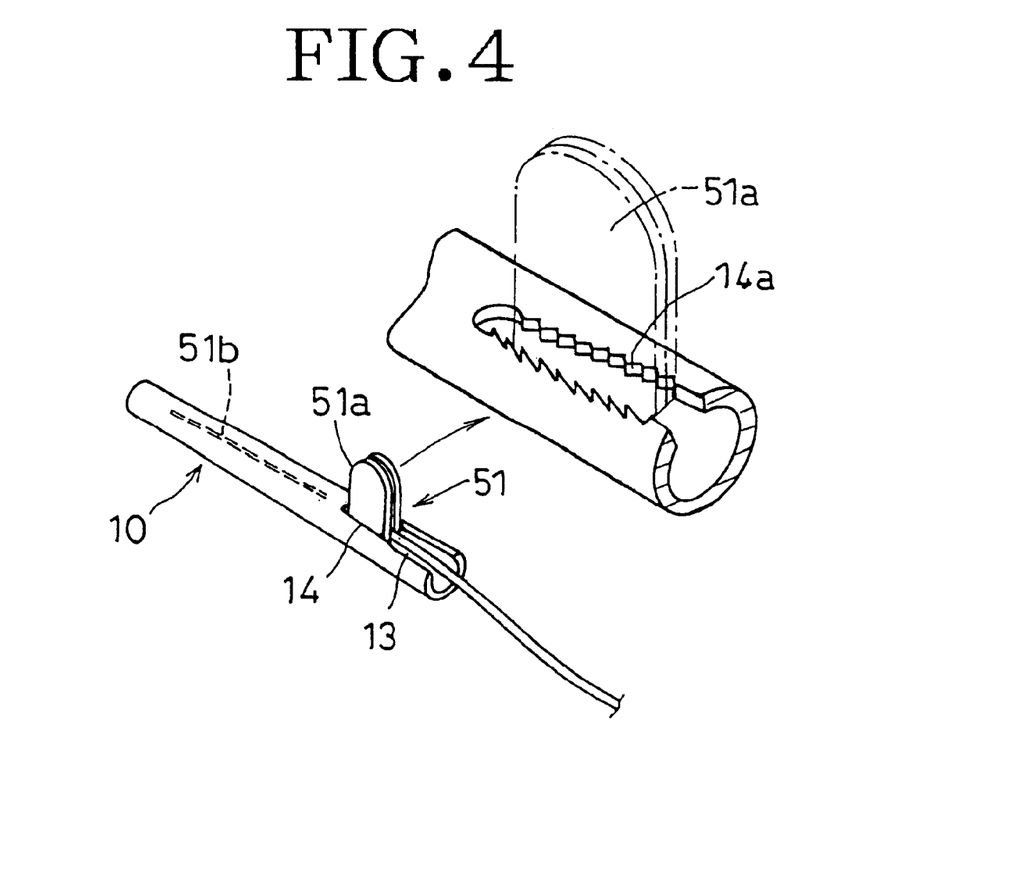
FIG. 4 is a diagram showing a state wherein the protecting cap of FIG. 1 has been attached to a winged needle.

In the case of a winged needle 51, as shown in FIG. 4, a needle 51*b* is inserted through the insertion notch 13 and slid forward, and a wing portion 51*a* is held in the slit 14 so as to attach the winged needle 51 to the protecting cap 10. The slit 14 is provided with a serrate fall-out preventing portion 14*a* to prevent the wing portion 51*a* from falling out easily.

Thus, using the protecting cap 10 of the embodiment allows the ordinary injection needle 50 and the winged needle 51 to be attached to the protecting cap 10 without largely moving the needles 50*b* and 51*b* in directions of the axes thereof.

Figure 5:
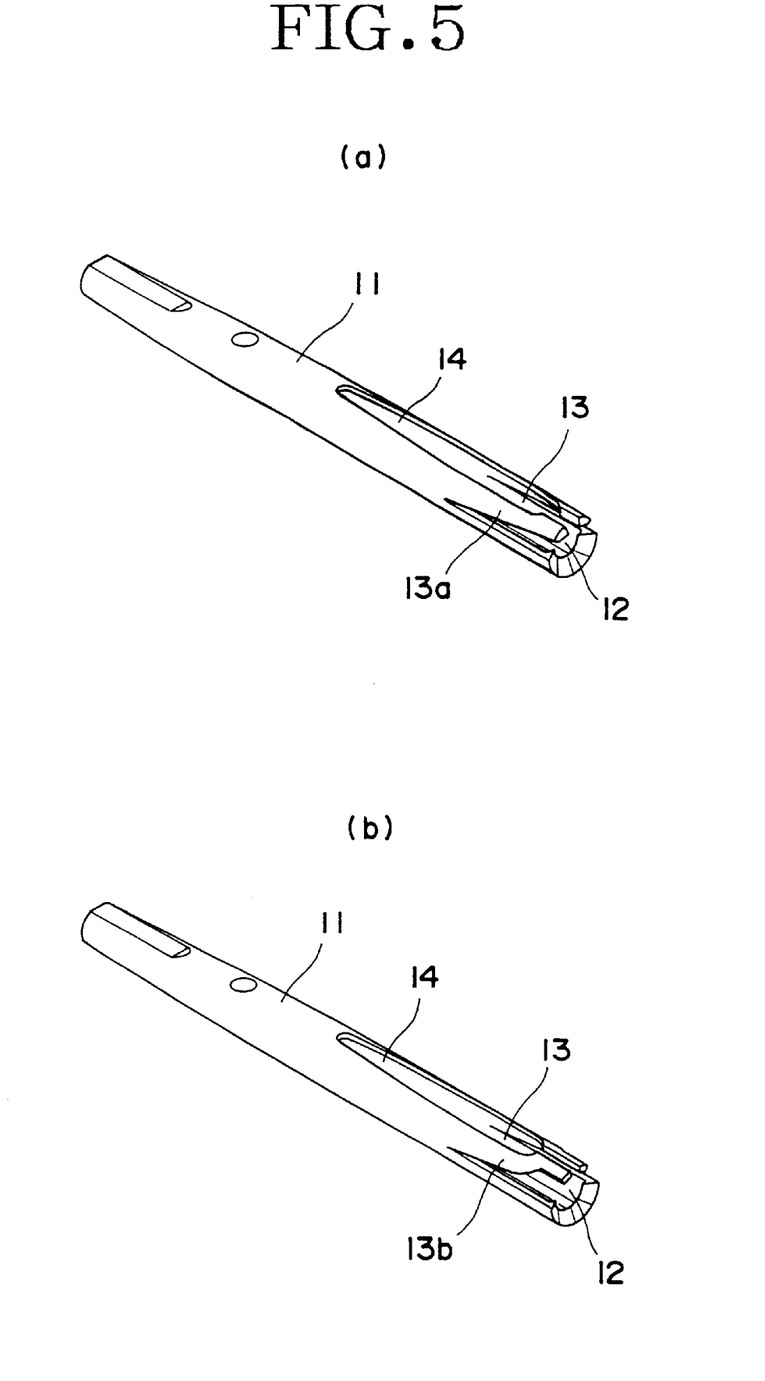
FIG. 5 provides perspective views showing embodiments in which shapes of an insertion port and an insertion notch of the protecting cap of FIG. 1 have been changed.

FIG. 5 shows embodiments in which the shapes of the insertion port 12 and the insertion notch 13 of the protecting cap 10 of FIG. 1 have been changed. FIG. 5(*a*) illustrates an embodiment in which a distal end of a locking portion 13*a* formed by extending an outer edge of the slit 14 is made thicker to form a narrow portion so as to prevent the injection needle 50 or the winged needle 51 from falling out easily. FIG. 5(*b*) illustrates an embodiment in which a gap at a distal end of a locking portion 13*b* formed by extending an outer edge of the slit 14 is made smaller to form a narrow portion so as to prevent the injection needle 50 or the winged needle 51 from falling out easily.

Figure 6:
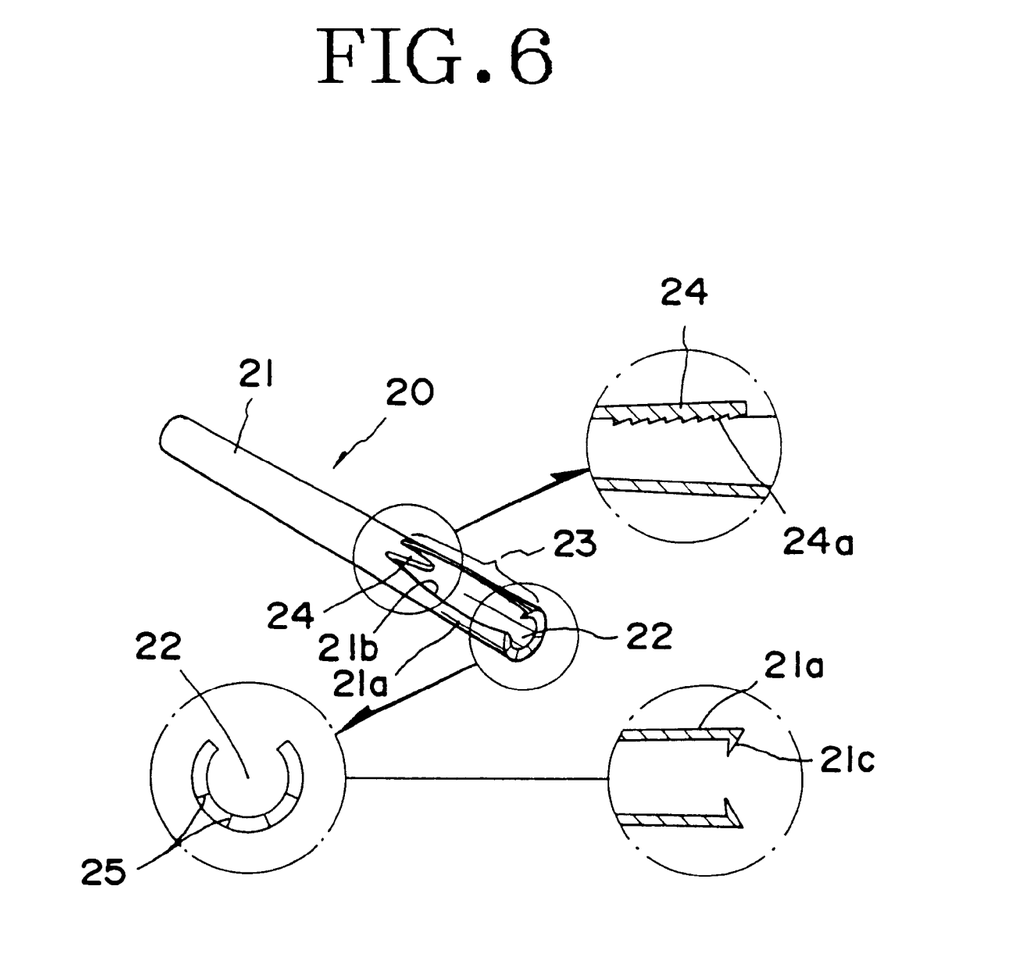
FIG. 6 is a perspective view showing a second embodiment of the needle protecting cap in accordance with the present invention.
Figure 7:
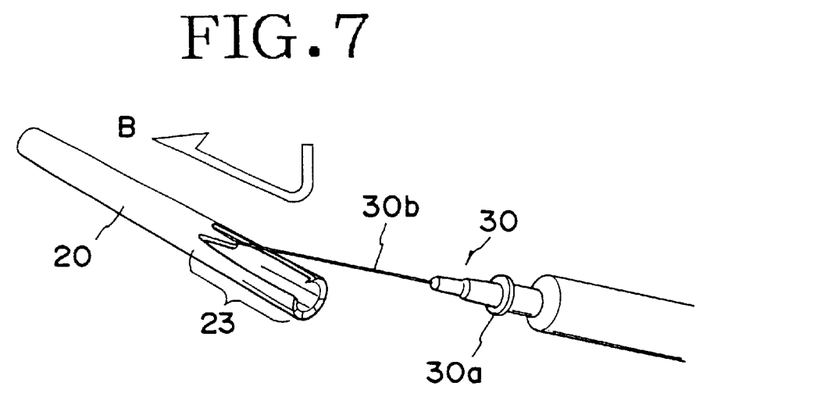
FIG. 7 is a schematic representation showing usage of the needle protecting cap of FIG. 6.
Figure 8:
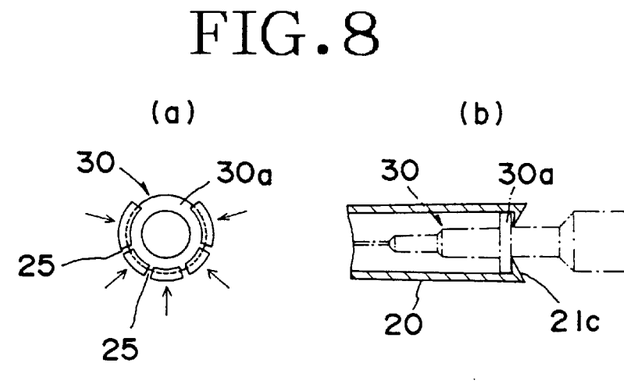
FIG. 8 is a diagram showing a state wherein the protecting cap of FIG. 6 has been attached to an injection needle.
Figure 9:
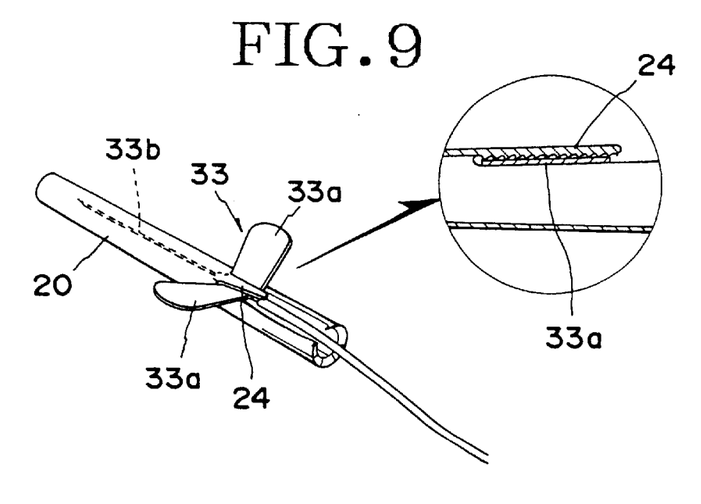
FIG. 9 is a diagram showing a state wherein the protecting cap of FIG. 6 has been attached to a winged needle.

FIG. 6 is a perspective view showing a second embodiment of the needle protecting cap in accordance with the present invention; FIG. 7 is a schematic representation showing usage of the needle protecting cap of FIG. 6; FIG. 8 is a diagram showing a state wherein an injection needle has been attached to the protecting cap; and FIG. 9 is a diagram showing a state wherein a winged needle has been attached to the protecting cap.

A needle protecting cap 20 of this embodiment is formed by cutting a part of a conventional protecting cap, and has an insertion notch 23 located in an upper surface of a tapered cylindrical body 21 and formed by longitudinally cutting a peripheral wall 21*a* inclusive of an insertion port 22 from the side of the insertion port 22 toward a distal end. In order to permit easy insertion of an injection needle, the length of the insertion notch 23 has been set to 40% of the cylindrical body 21 in this embodiment. A ridge line 21*b* of the peripheral wall 21*a* defining an outer edge of the insertion notch 23 is made of a downward curve to form a narrow portion at the insertion port 22. Furthermore, as shown in a partial enlarged sectional view of the drawing, an end surface 21*c* of the insertion port 22 is shaped like a hook. With this arrangement, the needle of the injection needle can be easily inserted through the insertion notch 23 while maintaining the size of the insertion notch 23, and the injection needle can be securely retained by the end surface 21*c* of the cap insertion port 22 to prevent the needle from falling out.

Reference numeral 24 denotes a locking portion for locking a winged needle which is formed at a distal end of the insertion notch 23 and oriented toward the insertion port 22. In this embodiment, the locking portion 24 is elastic, thereby enabling the wings of the winged needle to be held between the cylindrical body 21 and locking portion 24 to lock the wings. Reference numeral 24*a* denotes a serrate fall-out preventing portion formed on an inner surface of the locking portion 24 so that it is inclined in an inserting direction. This makes it possible to effectively prevent an attached winged needle from falling out. Reference numeral 25 shown in the partial enlarged view of FIG. 6 denotes a slit formed in a peripheral wall adjacent to the insertion port 22 of the cylindrical body 21. Forming the slit 25 allows an end portion of the insertion port 22 to be resiliently spread so as to permit easy insertion of a proximal end 30a of an injection needle 30 regardless of the size of the injection needle. (See FIG. 8).

In an injection needle of an ordinary syringe, as shown in FIG. 6 and FIG. 7, a needle 30b of the injection needle 30 is placed above the insertion notch 23, and, in this state, the needle 30b is moved in a direction at right angle to an axis of the injection needle 30 and inserted into the protecting cap 20 through the insertion notch 23. The injection needle 30 is further slid toward the distal end of the protecting cap 20 (in a direction indicated by an arrow B of FIG. 7) and attached to the protecting cap 20.

In the case of a winged needle 33, the needle 33b is inserted through the insertion notch 23 and slid forward to hold a wing portion 33a between a locking portion 24 and the peripheral wall 21a of the cylindrical body 21, thereby setting the needle as shown in FIG. 9.

Thus, using the protecting cap 20 of the embodiment allows the injection needle 30 and the winged needle 33 to be attached to the protecting cap 20 without considerably moving the needles 30b and 33b of the ordinary injection needle 30 and the winged needle 33 in directions of the axes thereof. Hence, the conventional accidental needle piercing of fingers, which are holding the cap, can be prevented.

FIG. 8 is a diagram showing the ordinary injection needle 30 attached to the protecting cap 20. As illustrated in (a) of the drawing, even if the proximal end 30a of the injection needle 30 is slightly larger, the slits 25 formed in the peripheral wall on the side of the insertion port 22 of the cylindrical body 21 spread to adjust to it. Moreover, since the end surface 21c of the insertion port 22 is shaped like a hook as illustrated in (b) of the drawing, the proximal end 30a of the injection needle 30 can be retained by the end surface 21c to hold the injection needle 30 so as to prevent the needle 30 from falling out.

Figure 10:
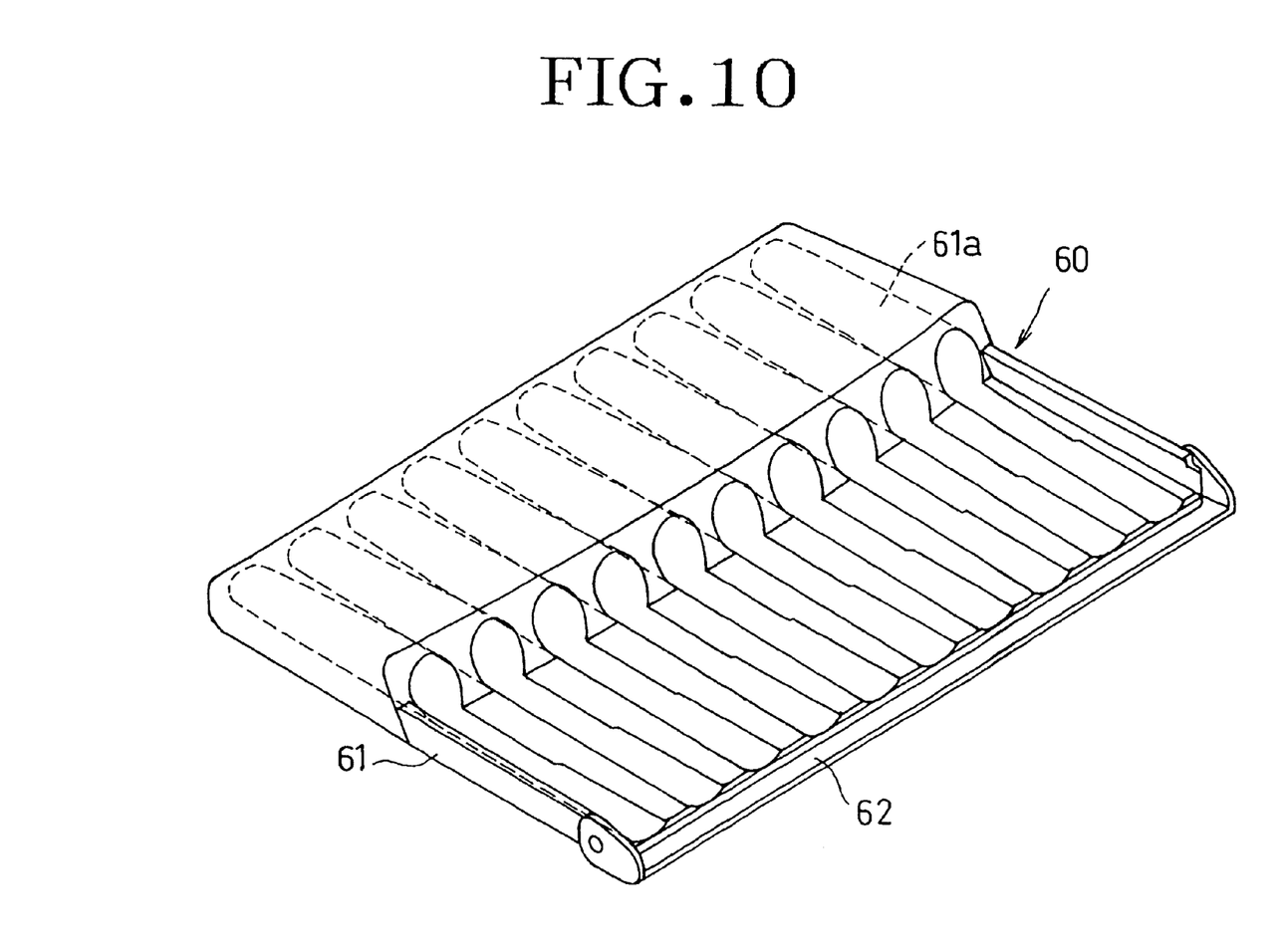
FIG. 10 is a perspective view showing a first embodiment of a needle disposal instrument in accordance with the present invention.
Figure 11:
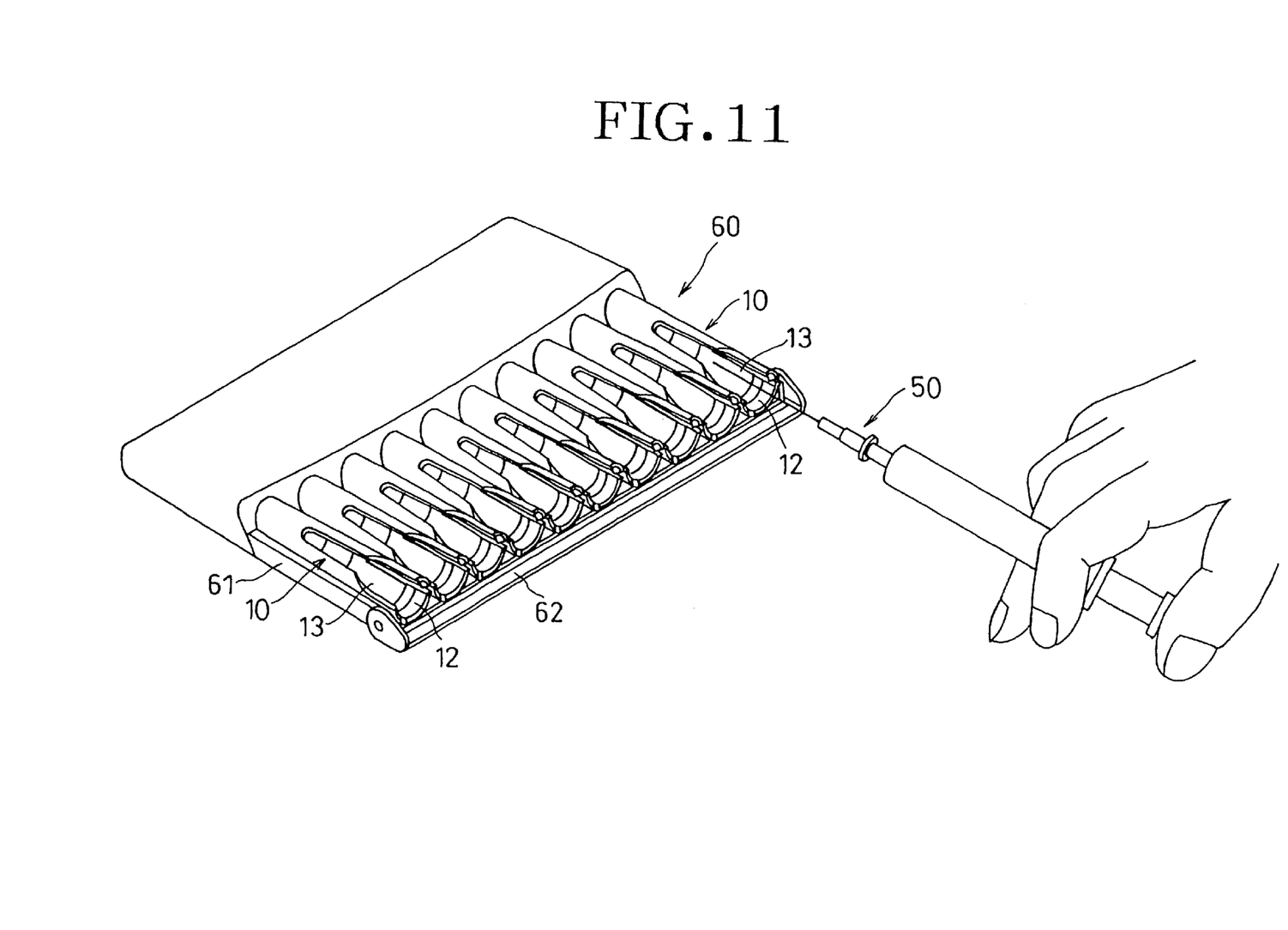
FIG. 11 is a perspective view showing the needle disposal instrument of FIG. 10 in use.

FIG. 10 is a perspective view showing a first embodiment of a needle disposal instrument in accordance with the present invention, and FIG. 11 is a perspective view showing the needle disposal instrument of FIG. 10 in use. Both FIG. 10 and FIG. 11 illustrate a state wherein a cover for preventing a protecting cap from falling out is open.

A needle disposal instrument 60 of this embodiment accommodates a needle protecting cap having an insertion port at one end thereof and composed of a cylindrical body capable of holding an injection needle. In this embodiment, descriptions will be given on an assumption that the protecting cap 10 shown in FIG. 1 is accommodated. In the needle disposal instrument 60, an open/close cover 62 for preventing protecting caps from falling out is installed to a case body 61 for holding the protecting caps 10 in such a posture that allow the used injection needle 50 to be inserted through the insertion port 12 of the needle protecting cap 10 as shown in FIG. 11.

The needle disposal instrument 60 is capable of holding ten protecting caps 10. One end of the case body 61 is provided with a cylindrical body holding section 61a for holding distal ends of the protecting caps 10, while the other end is provided with the open/close cover 62. In this embodiment, the open/close cover 62 is a short cover that is sufficient for covering the insertion port 12 to prevent the protecting caps from falling out. As an alternative, however, the cover may be formed so that its covering portion extends to the insertion port 12 and a part of the insertion notch 13 of the protecting cap 10.

The usage of the needle disposal instrument 60 will be described. Before use, the needle disposal instrument 60 is in a state wherein the protecting caps 10 have been accommodated in the case body 61, and the open/close cover 62 is closed. When using the needle disposal instrument 60, that is, when attaching an injection needle to the protecting cap 10, the open/close cover 62 is opened, and the needle 50b of the ordinary injection needle 50 or the needle 51b of the winged needle 51 is attached to the protecting cap 10 according to the procedure described in conjunction with FIG. 3 and FIG. 4. Upon completion of the attaching, the open/close cover 62 is closed. For attaching the next injection needle, the foregoing procedure is repeated. When all of the ten protecting caps 10 are filled, the protecting caps 10 are taken out of the needle disposal instrument 60 and placed in another container.

Thus, the needle disposal instrument 60 of this embodiment is formed so as to hold the protecting caps 10 in such a posture that allows the used injection needles 50 or winged needles 51 to be inserted through the insertion ports 12 of the needle protecting caps 10. Hence, the injection needle 50 or the winged needle 51 can be attached to the needle protecting cap 10 by holding the injection needle 50 or the winged needle 51 by one hand, while holding the case body 61 of the needle disposal instrument 60 by the other hand. Therefore, a distance between the injection needle 50 or the winged needle 51 and the fingers holding the case body 61 can be kept, making it possible to prevent accidental needle piercing.

In the above embodiment, the case body 61 is used by holding it by a hand. Alternatively, however, a stand may be provided for the case body 61 to support itself on a table or the like. Providing the stand eliminates chances of hands or fingers being positioned in front of injection needles or winged needles when attaching the injection needles or the winged needles to the protecting caps, thus permitting accidental needle piercing to be prevented further securely.

Figure 12:
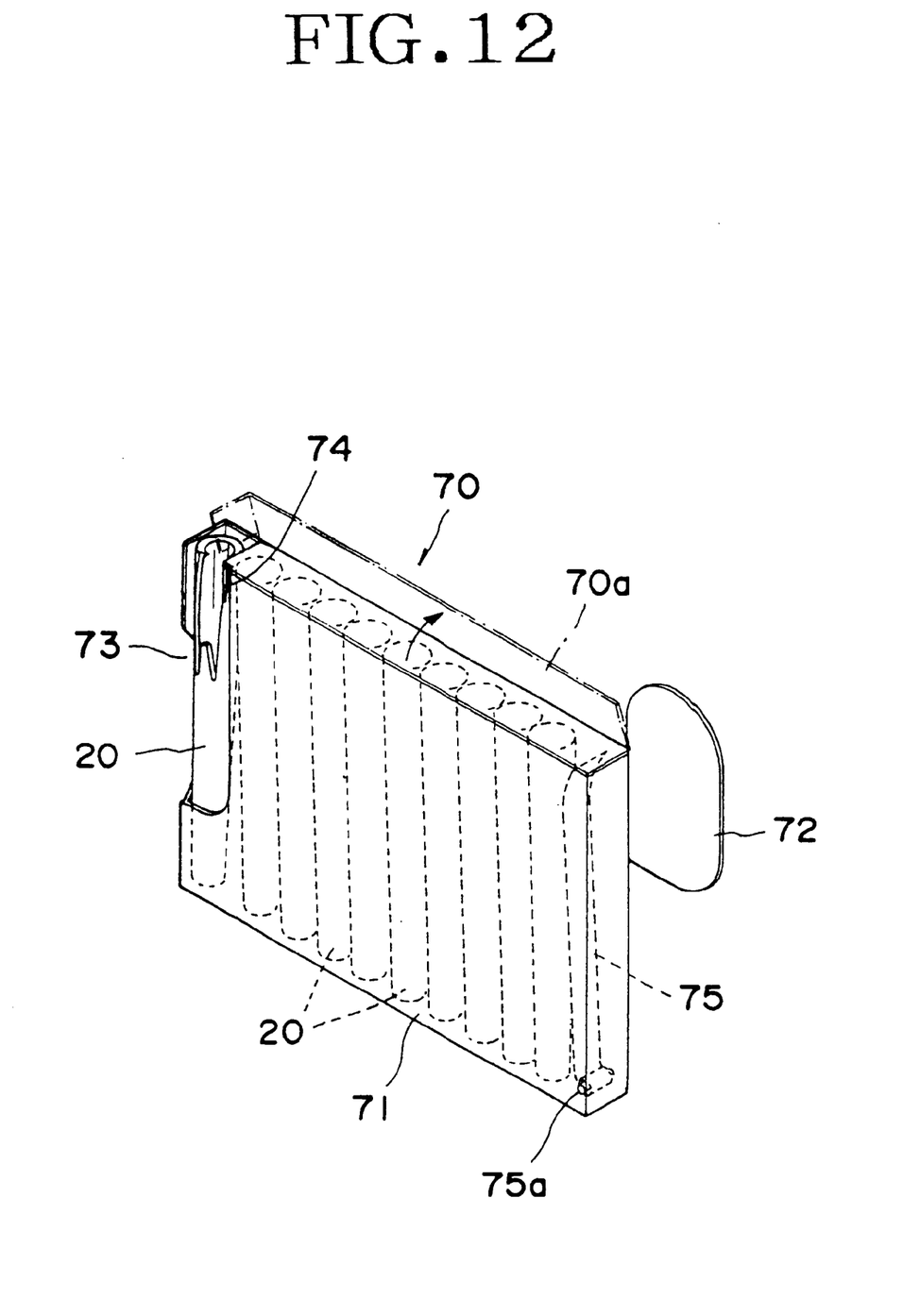
FIG. 12 is a perspective view showing a second embodiment of the needle disposal instrument in accordance with the present invention.
Figure 13:
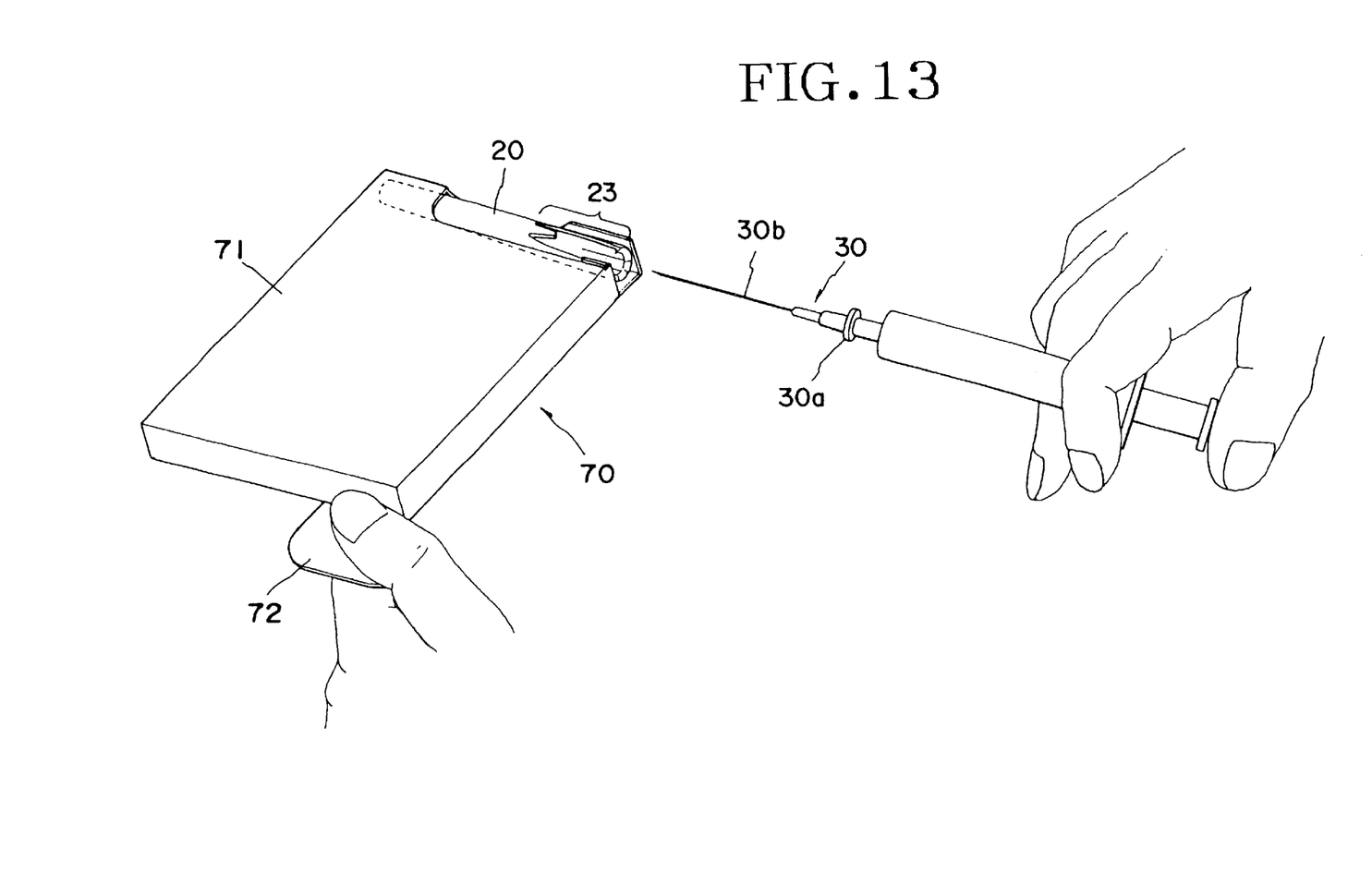
FIG. 13 is a perspective view showing the needle disposal instrument of FIG. 12 in use.

FIG. 12 is a perspective view showing a second embodiment of the needle disposal instrument in accordance with the present invention, and FIG. 13 is a perspective view showing the needle disposal instrument of FIG. 12 in use.

A needle disposal instrument 70 of this embodiment accommodates a needle protecting cap comprising a cylindrical body having an insertion port at one end thereof and capable of holding an injection needle. In this embodiment, descriptions will be given on an assumption that the protecting cap 20 shown in FIG. 6 is accommodated. The needle disposal instrument 70 is equipped with a box-shaped case body 71, and a thin-wall holding portion 72 which can be held by fingers is formed on the case body 71 as shown in FIG. 12. Reference numeral 73 denotes a removal port formed on the opposite side from the holding portion 72. From the removal port 73, the needle protecting caps 20 accommodated in the case body 71 can be taken out one by one in sequence by an operation of a spring 75 provided adjacently to the holding portion 72 of the case body 71.

Reference numeral 74 is an elastic return-proof portion which is formed on an upper part of the removal port 73. The portion 74 is elastically deformed toward the removal port 73 by an urging force of the spring 75 to feed the needle protecting cap 20 into the removal port 73, and also prevents the needle protecting cap 20 which was fed into the removal port 73 from moving back. The spring 75 has a mounting shaft 75a in a corner of the case body 71, and is urged toward the removal port 73.

In the needle disposal instrument 70 according to this embodiment, with the protecting cap 20 held in the case body 71, an ordinary injection needle 30 or a winged needle 33 is attached to the protecting cap 20 according to the procedure described above, and then only the protecting cap 20 to which the injection needle 30 or the winged needle 33 has been attached can be removed from the case body 71. This causes the protecting cap 20 held in the case body 71 to be pushed out into the removal port 73 by the spring 75, permitting the next injection needle 30 or the winged needle 33 to be attached in order. When all of the protecting caps 20 accommodated in the case body 71 have been used, a cover 70a of the case body 70 is opened, and the protecting caps 20 are supplied.

Thus, the needle disposal instrument 70 of this embodiment permits successive use and also permits the injection needle 30 or the winged needle 33 to be attached to the protecting cap 20 while holding the case body 71 or the holding portion 72 provided on the case body 71 by a hand. Hence, a distance between the injection needle 30 or the winged needle 33 and the fingers holding the case body 71 can be kept, contributing to the prevention of accidental needle piercing.

In the case of this embodiment, a stand may also be provided for the case body 71 to support itself on a table or the like.

The present invention provides the following advantages:

(a) The peripheral wall, which includes the insertion port, of the needle protecting cap formed of a cylindrical body having the insertion port on one end and capable of holding an injection needle is notched longitudinally from the side of the insertion port toward the distal end, and the slit for locking a winged needle is formed from the distal end of the notch toward the other end of the cylindrical body, or the locking portion for locking the winged needle which is oriented toward the insertion port is formed at the distal end of the notch. With this arrangement, both ordinary injection needles and winged needles can be placed in the protecting caps without largely moving the injection needles and the winged needles in their axial directions, thus permitting prevention of accidental finger piercing with conventional protecting caps designed to be held by fingers.

(b) The slits that can be expanded in a direction in which the insertion port spreads are formed in the peripheral wall of the insertion port. With this arrangement, the end portion adjacent to the insertion port can be elastically expanded, allowing the proximal end of a needle to be easily inserted regardless of the size of the injection needle, and the needle can be securely retained at the insertion port so that the needle does not fall out.

(c) The ridge line of the peripheral wall which defines an outer edge of the notch provides the narrow portion at the insertion port, allowing the needle to be securely retained at the cap insertion port so that the needle does not fall out.

(d) The slits or the locking portions are provided with fall-out preventing portions so that a winged needle can be effectively prevented from falling out after the needle has been attached.

(e) The notch and the slits at the insertion port, or the notch and the locking portion at the insertion port, are formed by partly cutting the cylindrical body. This arrangement permits easy mass production utilizing conventional products.

(f) The needle disposal instrument is provided with the case body that accommodates a plurality of needle protecting caps, each of the needle protecting caps being formed of the cylindrical body having an insertion port at one end thereof and capable of holding an injection needle, and holds the needle protecting caps in such a posture that used injection needles can be inserted from the insertion ports, and further provided with the means for preventing the needle protecting caps attached to the case body from falling out. By using this needle disposal instrument, an injection needle or a winged needle can be attached to the needle protecting cap by holding the injection needle or the winged needle by one hand, while holding the case body by the other hand. Therefore, a distance between the injection needle or the winged needle and the fingers holding the case body can be kept, making it possible to prevent accidental needle piercing.

(g) The open/close cover provided on the case body makes it possible to prevent the protecting caps from falling out and also to prevent injection needles attached to the protecting caps from falling out.

(h) The needle disposal instrument has a case body which maintains a posture of the accommodated needle protecting caps so that notches of the needle protecting caps are exposed for allowing used injection needles to be inserted and having a removal port through which the needle protecting caps can be taken out one by one and urging means for urging the accommodated needle protecting caps toward the removal port. This arrangement permits successive use, and also enables an injection needle or a winged needle to be attached to the protecting cap while holding the case body or the handle provided on the case body by a hand. Hence, the distance between the injection needle or the winged needle and the fingers holding the case body can be maintained, thus contributing to prevention of the accidental needle piercing.

(i) The handle formed on the case body makes it easy to attach an injection needle or a winged needle to the protecting cap.

(j) The stand provided to enable the case body to support itself eliminates chances of hands or fingers being positioned in front of injection needles or winged needles when attaching the needles to the protecting caps, thus permitting accidental needle piercing to be prevented further securely.

Industrial Applicability

As set forth above, the needle protecting cap in accordance with the present invention can be applied to winged injection needles in the same manner as in ordinary injection needles, which has been impossible with conventional protecting caps. The needle disposal instrument is suitably used for achieving efficient storage of protecting caps and efficient disposal of a large quantity of injection needles at large hospitals or the like where hundreds of injections are carried out daily.

What is claimed is:

1. A needle disposal instrument comprising a case body which accommodates a plurality of needle protecting caps, each of the needle protecting caps being formed of a cylindrical body having an insertion port at one end thereof and capable of holding an injection needle, and holds the needle protecting caps in such a posture that used needles can be inserted from the insertion ports, and means for preventing the needle protecting caps attached to the case body from falling out.

2. A needle disposal instrument according to claim 1, wherein said means for preventing fall-out is an open/close cover fitted to the case body on a side of the insertion ports for the needle protecting caps accommodated in the case body.

3. A needle disposal instrument according to claim 1, wherein said case body further comprises a handle.

4. A needle disposal instrument according to claim 1, further comprising a stand for the case body to support itself.

5. A needle disposal instrument comprising a case body, a plurality of needle protecting caps, each of the needle protecting caps being formed of a cylindrical body having an insertion port at one end thereof and capable of holding an injection needle, said case body having accommodating parts for receiving and accommodating the needle protecting caps on said case body in such a posture that a used needle can be inserted into each needle protection cap via the insertion port while the needle protecting cap is accommodated on said case body, and a preventing device movably mounted on said case body between an open position and a closed position, said preventing device in said open position enabling said accommodating parts to receive said needle protecting caps, said preventing device in said closed position preventing the needle protecting caps and the used needles from falling out of said case body.

6. A needle disposal instrument according to claim 5, wherein said needle protecting caps have a longitudinally extending elongated notch, said case body having an open position exposing said notch to thereby enable insertion of said needle into said protecting cap by moving said needle laterally through said exposed notch.

7. The needle disposal instrument according to claim 5, wherein each of said needle protecting caps comprises a peripheral wall inclusive of the insertion port being cut from a side of the insertion port toward a distal end to form a longitudinal elongated notch, and a slit for locking a winged needle formed to extend from a distal end of the notch toward the other end of the cylindrical body, said slit being provided with a fallout preventing portion, said case body having an open portion exposing said longitudinally elongated notch to thereby enable insertion of said used needle into said needle protecting cap by moving said used needle laterally through said exposed longitudinal elongated notch.

8. The needle disposal instrument according to claim 5, wherein each of said needle protecting caps comprises a peripheral wall inclusive of the insertion port being cut from a side of the insertion port toward a distal end to form a longitudinal elongated notch, and a locking portion for locking a winged needle which is oriented toward the insertion port being formed at a distal end of the notch, said case body having an open portion exposing said longitudinal elongated notch to thereby enable insertion of said used needle into said needle protecting cap by moving said used needle laterally through said exposed longitudinal elongated notch.

9. A needle disposal instrument according to claim 5 comprising a pivot movement for pivotably mounting said preventing device for movement between said open and closed positions.

10. A needle disposal instrument according to claim 5 wherein said preventing device is disposed in superimposed relationship with said needle protection caps and with said used needles when said preventing device is in said closed position.

11. A needle disposal instrument according to claim 10 wherein said preventing device is displaced from being in superimposed relationship with said needle protection caps and with said accommodating parts when said preventing device is in said open position.

12. A needle disposal instrument according to claim 5 wherein said preventing device includes a generally flat member free of apertures which is disposed in a first orientation when said prevention device is in said closed position, said flat member when in said first orientation generally overlying said needle protection caps and said used needles.

13. A needle disposal instrument according to claim 12 wherein said flat member is disposed in a second orientation when said prevention device is in said open position, said flat member when in said second orientation being displaced from overlying said needle protection caps and said used needles.

14. A needle disposal instrument according to claim 13 wherein said first orientation of the flat member is generally perpendicular to the second orientation of the flat member.

* * * * *

UNITED STATES PATENT AND TRADEMARK OFFICE
CERTIFICATE OF CORRECTION

PATENT NO.    : 6,409,705 B1
DATED         : June 25, 2002
INVENTOR(S)   : Chikashi Kondo It is certified that error appears in the above-identified patent and that said Letters Patent is hereby corrected as shown below:

<u>Title page,</u>
Insert the Foreign Application Priority Data information as follows:

-- [30]  Foreign Application Priority Data
         August 7, 1997  (JP) . . . . . . . . . . . . . . . . 9-213490 --

Signed and Sealed this

Twenty-second Day of October, 2002

Attest:

Attesting Officer

JAMES E. ROGAN
*Director of the United States Patent and Trademark Office*